US006810753B2

(12) United States Patent
Valdevit et al.

(10) Patent No.: US 6,810,753 B2
(45) Date of Patent: Nov. 2, 2004

(54) DISPLACEMENT TRANSDUCER (75) Inventors: Antonio Valdevit, Strongsville, OH (US); Helen Kambic, Solon, OH (US); Theodore Elster, Brecksville, OH (US); Ahmed El-Said, Lyndhurst, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 274 days.

(21) Appl. No.: 09/938,385

(22) Filed: Aug. 24, 2001

(65) Prior Publication Data

US 2002/0050174 A1 May 2, 2002

Related U.S. Application Data (60) Provisional application No. 60/228,649, filed on Aug. 29, 2000.

(51) Int. Cl.$^7$ .............................. G01L 1/22; G01L 1/04
(52) U.S. Cl. .............................. 73/862.045; 73/862.451
(58) Field of Search ..................... 73/862.045, 862.391, 73/862.451, 795; 338/6

(56) References Cited

U.S. PATENT DOCUMENTS

| | | | |
|---|---|---|---|
| 2,815,424 A | * 12/1957 | Painter | |
| 3,268,845 A | 8/1966 | Whitmore | |
| 3,272,003 A | * 9/1966 | Harting | .......................... 73/91 |
| 3,323,092 A | * 5/1967 | Balazs et al. ................... 338/6 |
| 3,433,060 A | * 3/1969 | Ives et al. ...................... 73/774 |
| 4,038,868 A | * 8/1977 | Heggie ........................... 338/4 |
| 4,141,349 A | 2/1979 | Ory et al. | |
| 4,444,205 A | 4/1984 | Jackson | |
| 4,649,933 A | 3/1987 | Jackson | |
| 4,699,010 A | 10/1987 | Klas et al. | |
| 4,715,235 A | 12/1987 | Fukui et al. | |
| 5,079,535 A | * 1/1992 | Neuman et al. ................ 338/2 |
| 5,086,785 A | 2/1992 | Gentile et al. | |
| 5,109,707 A | 5/1992 | VanGerpen | |
| 5,280,265 A | 1/1994 | Kramer et al. | |
| 5,289,722 A | * 3/1994 | Walker et al. ......... 33/DIG. 13 |
| 5,306,873 A | * 4/1994 | Suzuki et al. ................ 174/250 |
| 5,347,871 A | 9/1994 | D'Andrea et al. | |
| 5,652,395 A | 7/1997 | Hirano et al. | |
| 5,665,922 A | 9/1997 | Tsukada et al. | |
| 5,742,222 A | * 4/1998 | Young et al. ................... 338/2 |
| 5,813,406 A | 9/1998 | Kramer et al. | |
| 5,983,729 A | 11/1999 | Taylor | |
| 6,035,274 A | 3/2000 | Kramer et al. | |
| 6,127,672 A | 10/2000 | Danisch | |
| 6,148,675 A | * 11/2000 | Okano .......................... 73/763 |

FOREIGN PATENT DOCUMENTS

| | | |
|---|---|---|
| DE | 26 47 780 A | 4/1978 |
| DE | 35 28 052 A | 2/1987 |
| EP | 227 036 A | 7/1987 |
| EP | 0452573 A1 * 10/1991 ............ G01N/3/06 |

OTHER PUBLICATIONS

Kear et al. (1975) A method for recording tendon strain in sheep during locomotion, Aeta ortoph Scand 46, p. 896–905.*

Notebook Experiment No. 14—The Geometry; *A Simple Demonstration of Strain Geometry*, Web pp. 1–8, dated Oct. 1991, http://www.measurementsgroup.com/guide/notebook/e14/e14a.htm.

Mary Kear & R. N. Smith, *A Method for Recording Tendon Strain in Sheep During Locomotion*, Aeta orthop. Scand. 46, pp. 896–905, 1975.

(List continued on next page.)

*Primary Examiner*—Edward Lefkowitz
*Assistant Examiner*—Lilybett Martir
(74) *Attorney, Agent, or Firm*—Pearne & Gordon LLP (57) ABSTRACT

A displacement transducer capable of measuring very small displacements (on the order of 100 $\mu$m or less) comprises a strain gage mounted to the curved arc of a substrate. The transducer has a resolution of at least 10 $\mu$m, preferably at least 1 $\mu$m or better. The transducer can measure positive or negative displacement in a specimen and can also be used as an extremely sensitive load cell for very high resolution weight, load or mass determinations.

45 Claims, 5 Drawing Sheets

OTHER PUBLICATIONS

Donna L. Korvick et al., *The Use of an Implantable Force Transducer to Measure Patellar Tendon Forces in Goats*, Journal of Biomechanics, vol. 29, No. 4, pp. 557–561, 1996.

W. Herzog and E. M. Hasler, *Comment on "The Use of an Implantable Force Transducer to Measure Patellar Tendon Forces in Goats"*, Journal of Biomechanics, vol. 30, No. 3, p. 303, 1997.

E. S. Grood and D. L. Korvick, *Author's Response*, Journal of Biomechanics, vol. 30, No. 3, pp. 305–306, 1997.

J. L. Lewis et al., *A Note on the Application and Evaluation of the Buckle Transducer for Knee Ligament Force Measurement*, Journal of Biomechanical Engineering, vol. 104, pp. 125–128, May 1982.

Keith L. Markolf et al., *In Situ Calibration of Miniature Sensors Implanted Into the Anterior Cruciate Ligament Part I: Strain Measurements*, Journal of Orthopaedic Research, vol. 16, No. 4, pp. 455–463, 1998.

D. Barry and A. M. Ahmed, *Design and Performance of a Modified Buckle Transducer for the Measurement of Ligament Tension*, Journal of Biomechanical Engineering, May 1986, vol. 108, pp. 149–152.

Bruce D. Beynnon and Braden C. Fleming, *Anterior Cruciate Ligament Strain In–Vivo: A Review of Previous Work*, Journal of Biomechanics 31 (1998) pp. 519–525.

D. W. Hahs and R. N. Stiles, *Buckle Muscle Tension Transducer: What Does it Measure?*, Journal of Biomechanics vol. 22, No. 2, pp. 165–166, 1989.

W. S. Xu, et al., *Theoretical Analysis of an Inplantable Force Transducer for Tendon and Ligament Structures*[1], Journal of Biomechanical Engineering, vol. 114, May 1992, pp. 170–177.

Cobern V. Peterson, Jr. and Arthur B. Otis, *A Hall Effect Transducer for Measuring Length Changes in Mammilian Diaphragm*, Journal of Applied Physiology, 1983, pp. 635–641.

Jones M. H., et al., "A Method for Measuring Skin Tension" ISA Transactions, Instrument Society of America, Pittsburgh, US, vol. 27, No. 4, 1988, pp. 21–26.

* cited by examiner

DISPLACEMENT TRANSDUCER

CROSS-REFERENCE TO RELATED APPLICATIONS

This application claims the benefit of U.S. Provisional Patent Application Ser. No. 60/228,649 filed Aug. 29, 2000.

BACKGROUND OF THE INVENTION

1. Field of the Invention

The present invention relates to a displacement transducer. More particularly, the invention relates to a displacement transducer comprising a strain gage mounted to a curved arc of flexible material.

2. Description of Related Art

Strain gages are well known for measuring relative displacement in specimens. A typical strain gage is a variable resistance strain sensing element affixed to a strip of flexible backing material. Most commonly, the sensing element is an electrical conductor pathway arranged in an accordion pattern as known in the art. The strain gage is mounted to a specimen surface to measure displacement in the specimen.

A positive displacement in the specimen (i.e. an expansion) causes the gage to stretch. As a result, the electrical conductor pathway is also stretched which causes the diameter of the pathway to narrow. Because electrical resistance is inversely proportional to the diameter of the electrical pathway, this narrowing increases the resistance of the pathway as the gage is stretched. Positive displacement is measured by correlating the difference in potential ($\Delta V$) resulting from the change in resistance (positive $\Delta R$) to the magnitude of stretching.

Conversely, compression of the gage due to a negative displacement (i.e. compression of the specimen) increases the electrical pathway's diameter thus lowering its resistance. This reduction in electrical resistance (negative $\Delta R$) results in a negative change of potential which is correlated to the magnitude of the compression.

Further aspects and details of strain gage technology are set forth in the following references, the contents of which are incorporated herein by reference: A Method for Recording Tendon Strain in Sheep During Locomotion, Kear M., Smith R. N., Acta Orthop Scand, 46: 896–905, 1975; Theoretical Analysis of an Implantable Force Transducer (IFT) for Tendon and Ligament Structures, Xu W. S., Butler D. L., Stouffer D. C., Grood E. S., Glos D. L., Transactions of the ASME Journal of Biomechanical Engineering, 114: 170–177, 1992; In Situ Calibration of Miniature Sensors Implanted into the Anterior Cruciate Ligament Part I: Strain Measurements, Markolf K. L., Willems M. J., Jackson S. R. and Finerman G. A. M., Journal of Orthopaedic Research, 16:455–563, 1998; Anterior Cruciate Ligament Strain In-Vivo: A Review of Previous Work, Beynnon B. D., Fleming B. C., Journal of Biomechanics, 31: 519–525, 1998; A Note on the Application and Evaluation of the Buckle Transducer for Knee Ligament Force Measurement, Lewis J. L., Lew W. D., Schmidt J., Transactions of the ASME Biomechanical Engineering, 104: 125–128, 1982; Design and Performance of a Modified Buckle Transducer for Measurement of Ligament Tension, Barry D., Ahmed A. M., Transactions of the ASME Journal of Biomechanical Engineering, 108: 149–152, 1986; and Buckle Muscle Tension Transducer: What Does It Measure?, Hahs D. W., Stiles R. N., Journal of Biomechanics, 22:2, 165–166, 1989.

Existing strain gages perform adequately for measuring displacements on the order of 0.5–5% of the gage length. Beyond this range, non-linearities, noise and damage to the gage elements may occur. For a 5 mm strain gage, this range would be 25–250 $\mu$m. Gages for measuring very small displacements, on the order of 5 $\mu$m, suffer from several drawbacks. First, such strain gages are very small, perhaps 2 or 3 mm in length, and can often only measure displacements up to 5% or even 1% of their length without being damaged. For example, a 3 mm gage may only be able to measure a displacement of about 30 $\mu$m without damage. This is because the electrical conductor pathways have exceedingly small diameter (i.e. on the order of 1 $\mu$m) which are easily snapped if stretched beyond their mechanical limits.

Second, the $\Delta R$ for very small displacements is also very small. Hence, even a 3 mm gage with an upper displacement limit of 30 $\mu$m may have a resolution of only 5–10 $\mu$m (or 18–33% of scale), making accurate measurement in this range difficult to achieve. Resolution can be improved somewhat with electronic signal amplification and conditioning. However, these methods amplify noise as well as signal, and only marginal success has been achieved at measuring very small displacements.

Third, such small strain gages quickly experience nonlinear or exponential $\Delta R$ for very small displacements. Exponential $\Delta R$ will result in exponential $\Delta V$ output. Nonlinear or exponential output complicates gage calibration and further obscures accurate measurement of displacement.

There is a need in the art for a strain or displacement transducer that can measure very small displacements without suffering from the above shortcomings. Preferably, such a transducer will have very high resolution (down to 1 $\mu$m or better) at displacements of less than 100 $\mu$m, preferably less than 50 $\mu$m, will be able to measure displacements greater than 5% or even 10% of the strain gage length, and will have a substantially linear $\Delta R$ in that range.

SUMMARY OF THE INVENTION

A displacement transducer is provided having a substrate having a bridge and a strain gage securely mounted to the bridge. The strain gage is mounted to the bridge in a pre-stressed condition.

A displacement transducer is also provided having a substrate having a bridge and a strain gage securely mounted to the bridge, wherein the bridge is a polyfaceted arc.

A hoop strain device for measuring radial expansion of a femur or other bone is also provided. The hoop strain device comprises a flexible band and a displacement transducer. The flexible band is adapted to surround and be in intimate contact with a bone circumference. The displacement transducer is mounted on the flexible band, and comprises a substrate having a curved arc and a strain gage securely mounted to the curved arc.

DETAILED DESCRIPTION OF THE PREFERRED EMBODIMENTS OF THE INVENTION

In the description that follows, when a preferred range, such as 5 to 25 (or 5–25), is given, this means preferably at least 5, and separately and independently, preferably not more than 25.

Figure 1:
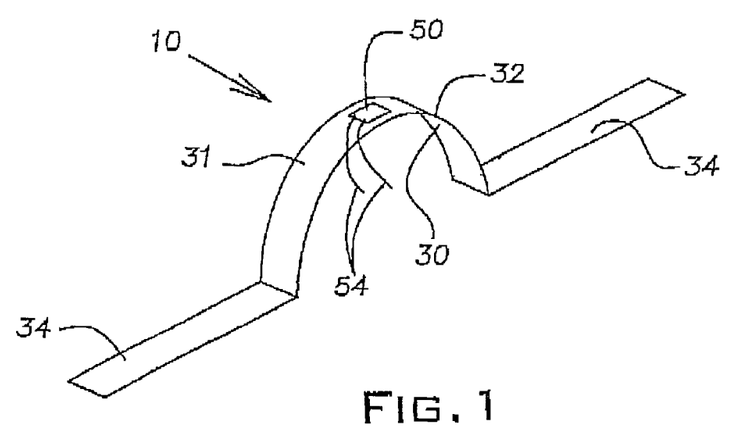
FIG. 1 is a perspective view of a first preferred embodiment of a displacement transducer according to the invention.
Figure 1A:
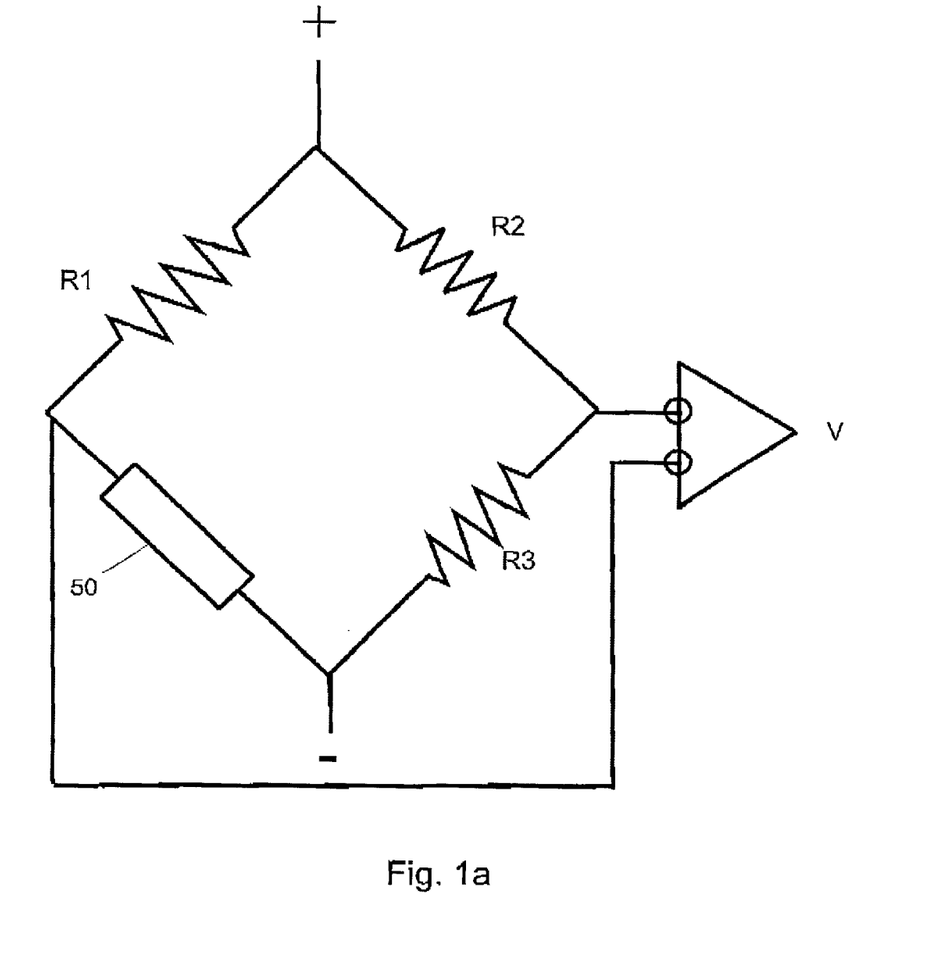
FIG. 1a shows schematically the strain gage of the invented displacement transducer connected in a Wheatstone bridge circuit.

Referring first to FIG. 1, a first preferred embodiment of the invented displacement transducer is shown. The transducer has a substrate 30 and a strain gage 50. The substrate is preferably a strip or length of flexible material having an arc portion or bridge 32 positioned between mounting tabs 34 on either side. The substrate may be formed from a thin, preferably flat strip of material having a substantially rectangular cross-section and a thickness preferably less than 0.05, preferably 0.01 inches, as in FIG. 1, or it may be formed from a material having some other cross-section; e.g. circular, less preferably pentagonal, hexagonal, octagonal, trapezoidal, less preferably some other cross-section.

Preferably, the arc portion or bridge 32 extends upward from mounting tabs 34 at either end and defines the circumference or perimeter of a geometric shape, such that arc portion or bridge 32 is displaced from or mechanically separated from the specimen of interest to which the transducer 10 is mounted. The arc portion or bridge 32 is preferably a curved arc as in the first preferred embodiment shown in FIG. 1, less preferably a rectilinear arc as in the second preferred embodiment shown in FIG. 4, less preferably a polyfaceted arc as shown in FIG. 5. Such a polyfaceted arc can have from 2–1000 or more discrete, uniform or nonuniform, flat or curved nirfaces or facets. The arc portion or bridge 32 of FIG. 5 has six facets for illustration. Preferably, the mounting tabs 34 are formed integrally with the arc portion or bridge 32, though it is not required. Tabs 34 may he formed separately and attached to ate portion or bridge 32 via conventional means.

FIG. 1 shows a first preferred embodiment of the invented transducer in which bridge 32 is a circular or curved arc 31 as above described. Preferably, arc 31 is a semicircle extending from mounting tabs 34 at either end, which are preferably formed integrally with arc 31. Substrate 30 is preferably made from metal, preferably brass, less preferably aluminum, tin, copper, silver, nickel, manganese, zinc, platinum, palladium, other metals, or alloys thereof. Less preferably, substrate 30 can be made from plastic, less preferably some other material having a suitable flexible modulus. It will be understood that the choice of material and cross-section (both shape and dimension) for the substrate will vary depending on the nature and magnitude of the displacement to be measured. A brass substrate 30 having a thin, substantially rectangular cross-section as in FIG. 1 is preferred in this embodiment because it has proven particularly well suited for measuring very small displacements. Brass is the preferred substrate for the following reasons: 0.015" strain gages are commonly available which are temperature compensated for brass, thus reducing, preferably eliminating, any temperature gradient between the gage 50 and the substrate 30; brass has been shown to effectively dissipate heat over the entire substrate surface, and measured displacement fluctuations after transducer equilibration are less than 1 $\mu$m after several (preferably at least 3, 4, 5, 6, 8, 10, 24, 36, 48, or 72) hours of operation; the density of brass is less than stainless steel which reduces inertial effects of the transducer during cyclic or high speed applications; brass is very corrosion resistant, significantly moreso than steel; and brass is ductile and will not fatigue from deformations of 10% of the span of bridge 32. Surprisingly, an invented transducer 10 having a brass substrate 30 has endured over 25 million expansion cycles without fatiguing during continuous use.

The strain gage 50 is securely mounted (for example via soldering, welding, cyanoacrylate glue, or similar means) to the curved arc 31 in this embodiment, preferably at the apex thereof. By apex, it is meant that the strain gage 50 be mounted at the distal-most point along arc 31 from the mounting tabs 34, preferably equidistant therebetween. Lead wires 54 extend from the gage 50 and are connected to a signal amplifier via a Wheatstone bridge circuit (not shown). optionally, as shown in FIG. 5, a small amplifier 60 which fits on one or more of the mounting tabs 34 or as part of a mounting tab, or which is integrated into the strain gage 50, can be used.

Most preferably, the strain gage 50 is soldered to the arc to ensure uniform intimate surface to surface contact between the strain gage 50 and the arc 31. Less preferably, the strain gage may be adhered to the arc via laser welding, adhesive, or less preferably some other known means. An invented transducer as described above can be used to precisely measure displacements from 1 $\mu$m or less, up to 10 meters or beyond. It will be understood that the measurable range of the invented transducer 10 will depend upon the size of the transducer.

An invented transducer for measuring very small displacements (i.e. on the order of 1, 2, 5, 10, 20, 30, 50, 80, 100, 250, 500, or 1000 $\mu$m), preferably is comprised and has dimensions as follows. The substrate (including the arc 31 and mounting tabs 34) are preferably brass shim stock, preferably 0.0001–0.1, preferably 0.001–0.05, preferably 0.002–0.01, preferably 0.003–0.009, preferably about 0.005, inches in thickness and 0.01–0.5, preferably 0.05–0.3, preferably 0.08–0.2, preferably 0.1–0.18, preferably 0.118–0.157, inches (the latter being 3–4 mm) in width. In a resting state, arc 31 is preferably circular, preferably a semicircle, and has a resting radius of preferably 2–10 mm (0.079–0.394 in), more preferably 2–5, mm (0.079–0.197 in). (Optionally, arc 31 can have a resting radius less than 2 mm, e.g. 0.5–1.9 mm, for measuring exceedingly small displacements on the order of 0.01–0.1 $\mu$m). When the substrate (including arc 31) is made of brass, the strain gage is preferably also made from brass or a material with expansion characteristics comparable to brass, or is otherwise substantially temperature compensated for brass. Generally, the strain gage is preferably made of a material having a coefficient of thermal expansion substantially similar to the coefficient of thermal expansion of the material of arc 31, or is otherwise substantially temperature compensated for the material of arc 31. The strain gage is preferably about 0.015, less preferably 0.01–0.02, less preferably 0.01–0.05, inches in length, and preferably has a resistance at rest of 1–1000, preferably 10–800, preferably 50–600, preferably 80–400, preferably 100–200, preferably 120, ohms, less preferably any measurable resistance.

Figure 2:
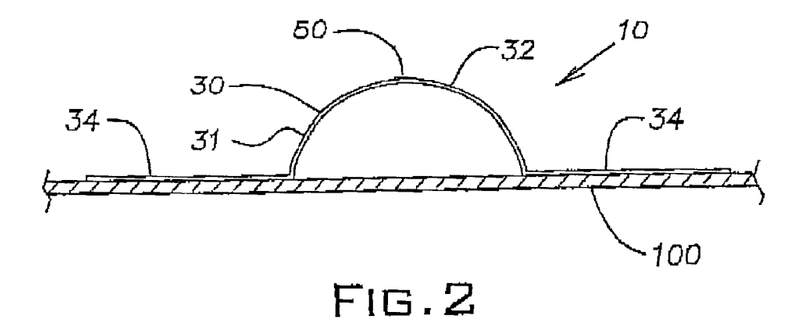
FIG. 2 is a side view of the transducer in FIG. 1, with the transducer mounted on a specimen.

A preferred strain gage having the above characteristics is Metal Foil Strain Gage, Product No. EA13-015LA-120 from Measurements Group, Inc., Raleigh, N.C. It will be understood by one skilled in the art that the length of the mounting tabs 34 is of little consequence so long as they are sufficiently long to allow secure attachment to the specimen of interest. The mounting tabs 34 are secured to the specimen 100 (see FIG. 2) via adhesive such as cyanoacrylate glue, krazy glue, adhesive tape, PSA, or the like, or soldering, welding, or other nondestructive means. Less preferably, tabs 34 may be mounted to the specimen via destructive means such as screws, nails, staples, and the like.

The strain gage has a flat or planar resting profile. Therefore, the gage is mounted to the arc 31 in a pre-stressed condition since gage 50 must bend or curve to conform to the arc surface to ensure intimate surface to surface contact as described above. Hence, strain gage 50 is pre-stressed at the resting or zero displacement condition of displacement transducer 10.

In operation, an electrical DC signal is passed through the gage to generate a resting output voltage which is passed to a quarter Wheatstone bridge circuit and subsequently amplified. The transducer is surface mounted via tabs 34 to the specimen of interest. As seen from FIGS. 2 and 3, deformation in the specimen 100 will cause the semicircular arc to experience elongation or compression. This change in the semicircle radius causes the electrical resistance of the strain gage mounted to the substrate surface to change, thereby generating a change in output voltage proportional to the deformation of the gage (and the substrate).

A displacement transducer having a substrate 30 as above described can measure much greater displacements than gage 50 alone applied directly to the specimen. For example, taking the preferred 0.015 inch (0.381 mm) gage and assuming an upper displacement limit of 10%, the gage could measure a maximum displacement of 0.038 mm or 38 $\mu$m before being damaged. Mounting that same 0.015 inch gage pre-stressed to an arc of 5 mm diameter, the theoretical maximum displacement that can be measured occurs when arc 31 is stretched completely flat. Mathematically, this distance is the arc length minus its initial diameter, which for a 5 mm semicircular arc is $[\frac{1}{2}\times(\pi\times D)-D]=[\frac{1}{2}\times(3.14\times 5$ mm$)-5$ mm$]=2.8$ mm or about 2800 $\mu$m. Because gage 50 is pre-stressed at the apex of the arc, flattening the arc reduces stress on the gage and presents no danger of damaging the gage. In practice, arc 31 could not be stretched until completely flat due to the sharp bends where the arc meets the mounting tabs 34 (though this problem could be somewhat minimized by using larger radius, less sharp bends). However, the invented transducer clearly can measure at least 1, preferably 2 orders of magnitude greater displacement using the same gage than the gage alone could measure if mounted directly to the specimen. A transducer according to the first preferred embodiment preferably can measure displacement at least 10, preferably 15, preferably 20, 30, 40, or 50, percent the length of gage 50.

In its pre-stressed condition, gage 50 preferably has a resistance of about 121 ohms, 1 ohm greater than the resting condition for the gage. The gage is connected to an amplifier via a Wheatstone bridge circuit as known in the art, the three other resistors of the bridge preferably being 120 ohm resistors. Such a configuration generates a non-zero voltage output signal from the bridge at zero displacement of the transducer 10 (the transducer's resting condition). A non-zero voltage output signal is preferred to zero voltage at zero displacement because noise and signal drift are statistically much less significant compared to a non-zero voltage output signal than to a zero voltage signal. Thus, a non-zero voltage signal at zero displacement makes zero, and very small displacements from zero, on the order of 1 $\mu$m, easier to accurately resolve.

It has also been found that a displacement transducer 10 as above described produces a much amplified $\Delta R$ response for a given specimen displacement compared to a surface-mounted strain gage alone. Without wishing to be bound by any particular theory, it is believed that an amplified $\Delta R$ (and resulting $\Delta V$ output signal) may result for one or more of the following reasons. As stated above, resistance of the electrical conductor pathway is inversely proportional to pathway diameter. As the pathway diameter decreases from stress, it approaches a yield condition at which point ultimately it will snap resulting in infinite resistance. From zero to low stress, well below the yield point, resistance varies linearly with stress. However, at some point prior to yield an inflection occurs in the resistance-stress curve. From this point until yield, resistance varies exponentially with stress. Beyond this inflection point, a given change in displacement, say 2 $\mu$m, will yield a far greater (exponentially greater) change in $\Delta R$ than below the inflection point.

Measurements Group, Inc., the manufacturer of the preferred strain gage, suggests that bending the gage to a curvature of less than 2 inches diameter should be avoided precisely to avoid transcending the inflection point. The strain gage 50 of an invented transducer preferably has a radius of curvature of about 0.079–0.394, preferably about 0.079–11197, inches, substantially equal to the preferred radius of arc 31. This small radius of curvature for gage 50 is contrary to what the manufacturer suggests precisely to pre-stress the gage so it will operate beyond its inflection point in the exponential range. So for a given displacement, the corresponding change in stress causes an exponential variance in resistance.

Though the resistance-stress function is not technically linear beyond the inflection point, substantially linear voltage output at very high resolution (i.e. 1 $\mu$m displacement) has been observed using an invented transducer; ($R^2$ values up to 0.9999 and higher have been observed for as many as 16 points spanning 300 $\mu$m of positive displacement). This is a surprising and unexpected result. The observed linearity is believed due to the fact that when the invented transducer is applied to measure small displacements (i.e. less than 40%, 30% or 20% the length of gage 50), the change in stress of gage 50 atop arc 31 is small enough that the resistance-stress function is approximately linear. A transducer using a pre-stressed strain gage can measure displacements far greater than the 5% gage length recommended by the manufacturer at very high resolution. The invented transducer preferably has a resolution smaller than or at least 10, preferably 8, preferably 5, preferably 4, preferably 2, preferably 1, $\mu$m.

Figure 3:
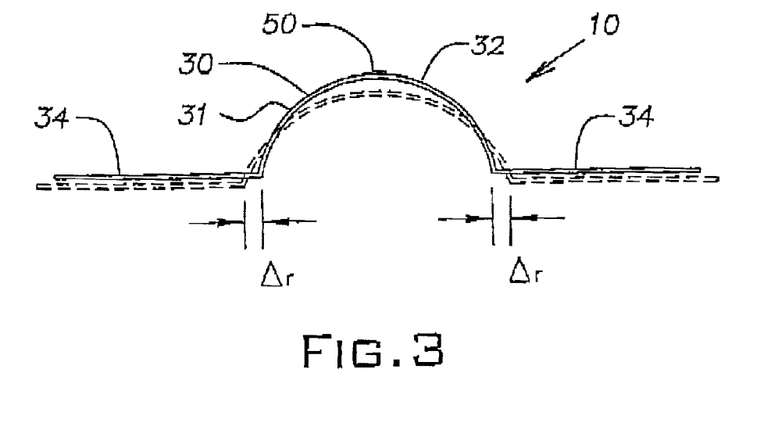
FIG. 3 is a side view of the substrate of the transducer of FIG. 1 comparing a resting configuration thereof (solid line) with a positive displacement configuration (broken line).

In addition to pre-stressing the strain gage, it is believed arc 31 also mechanically reduces the change in stress felt by the gage for a given specimen displacement. Referring to FIG. 3, the magnitude of the change in radius $\Delta r$ of arc 31

(and therefore gage 50) is substantially less than (approximately half) the corresponding displacement in the specimen $\Delta L$. As is apparent from the figure, this is because $\Delta L$ is equal to, or substantially equal to, $2 \times \Delta r$ assuming the arc 31 uniformly expands as the mounting tabs 34 are displaced. Uniform expansion of the arc 31 will occur so long as the arc has a substantially smooth curvature with no sharp bends, thus minimizing strain risers due to geometrical non-uniformities (i.e. sharp corners).

It is believed that the mechanical reduction in stress change felt by gage 50 cooperates with the exponential resistance-stress relationship for the pre-stressed gage to yield an amplified linear $\Delta R$ resulting in a substantially linear $\Delta V$ output signal for very small specimen displacements. This linear amplification occurs without electronic amplification or signal conditioning that can introduce artifact or noise into the output signal.

It is also believed that placement of the gage at the apex of arc 31 improves the accuracy of the transducer by mechanically focusing displacement-caused stress on the gage. For very small displacements, especially less than 100 $\mu$m, minute surface variations in the specimen can strongly affect uniformity of displacement (expansion or contraction). By mounting the strain gage at the apex of a curved arc 31, the effect of nonuniform specimen displacement is minimized. This is because arc 31 will expand uniformly regardless of whether only one or both mounting tabs 34 is/are being displaced relative to a fixed point. In other words, if one mounting tab is held in a fixed position while the other is displaced some distance, the gage 50 on top of the arc will measure the total displacement just as if both tabs 34 were equally displaced one half that distance. Thus, transducer 10 to some degree corrects for specimen nonuniformity when measuring very small displacements.

Figure 4:
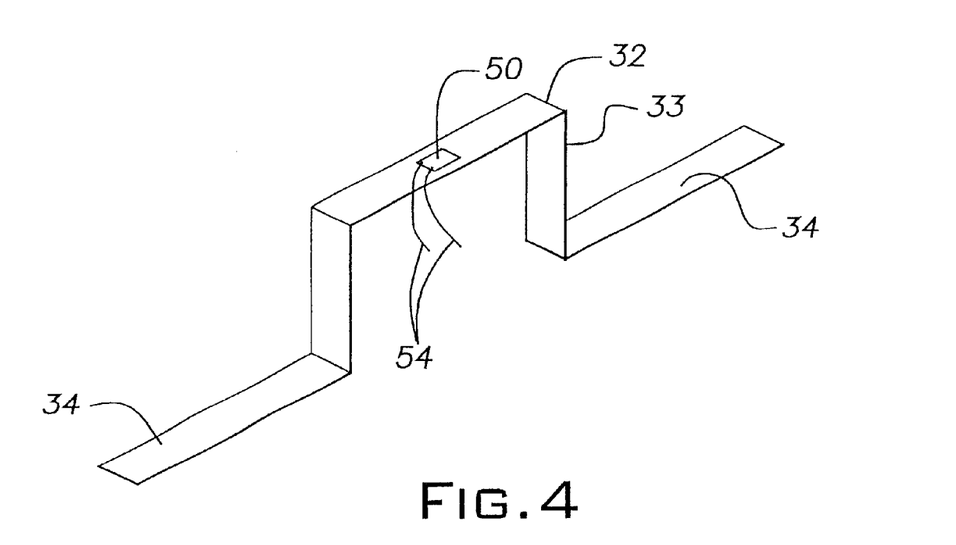
FIG. 4 is a perspective view of a second preferred embodiment of a displacement transducer according to the invention.
Figure 5:
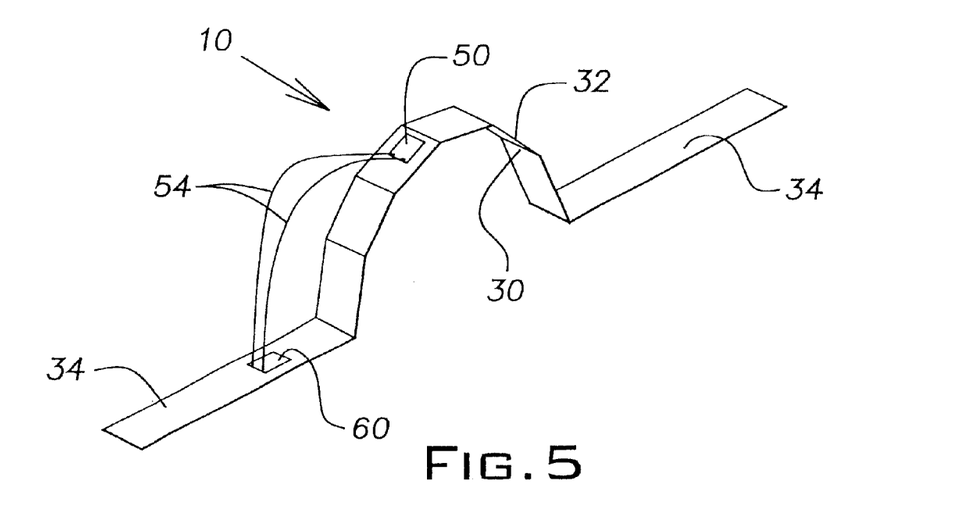
FIG. 5 is a perspective view of an invented displacement transducer having a substrate with a polyfaceted bridge having 6 facets.

Referring to FIG. 4, a displacement transducer according to a second preferred embodiment is shown. The difference from the first preferred embodiment is that the bridge 32 of substrate 30 is a square or rectilinear arc 33 instead of the curved arc 31 shown in FIG. 1. Strain gage 50 is mounted to the upper surface of the rectilinear arc 33 as shown in FIG. 4 similarly as described above for curved arc 31. Similarly to curved arc 31, the rectilinear arc 33 mechanically reduces the change in stress felt by the gage 50 for a given specimen displacement. A transducer according to the second preferred embodiment preferably can measure displacement at least 10, preferably 15, preferably 20, 30 or 40, percent the length of gage 50. It will be noted that gage 50 is not pre-stressed in this embodiment, and that the upper portion of rectilinear arc 33 becomes concave or convex respectively in response to a positive or negative specimen displacement. Therefore, stress to gage 50 is increased as the upper portion becomes more concave or more convex, and the benefits of a pre-stressed gage are not observed in this embodiment. Consequently, this embodiment is less preferred, and should only be used where space constraints prevent using a curved arc 31.

When applied to measure very small displacements (on the order of 100 $\mu$m, preferably 50 $\mu$m or less), the invented transducer 10 is of small geometry, preferably 5–40, preferably 6–30, preferably 7–20, preferably 8–12, mm in overall length and 1–25, preferably 2–20, preferably 3–10, preferably 4–6, mm in overall height. This facilitates placement of the transducer in confined areas for mounting onto a specimen. The transducer preferably has a small mass (preferably less than 2, preferably 1, preferably 0.8, preferably 0.5, preferably 0.3, preferably 0.2, grams) making it applicable for dynamic applications without the need for acceleration compensation due to inertial effects. The resolution and accuracy limits of the transducer are theoretically only limited by the equipment used to calibrate the transducer.

In addition to measuring displacement, the invented transducer can be calibrated in response to an applied load to provide an extremely sensitive load cell for applications requiring very high resolution measurement of very small loads. By applying calibration curves for both deformation and load to the transducer output, the transducer can function as a combined load/deformation transducer. Such a sensitive transducer can be applied, e.g., to the mechanical characterization of in-vivo soft tissues.

The transducer can be reused between experiments and applications simply by recalibrating in cases where excessive deformations were encountered. Calibration of the transducer to applied loads can also be performed to provide an extremely sensitive load cell in applications requiring small load application and measurement. Where extreme sensitivity in measuring larger loads (e.g. on the order of 1 kg, 10 kg, 100 kg, or greater) is required, an invented transducer can be provided having a substrate 30 in the form of a cylindrical rod having a circular cross-section, e.g. having a diameter of at least or at most 0.5, 1, 2, 3, 4, or 5, inches, or any other diameter suitable to provide a load cell that can be calibrated against a desired range of loads. Less preferably, a load cell as above described can have some other cross-section, e.g. square, rectangular, triangular, or trapezoidal. A circular cross-section is preferred because it has no sharp bends.

The invention will be better understood in conjunction with the following examples. These examples are provided by way of illustration only, and not limitation.

EXAMPLE 1

Figure 6:
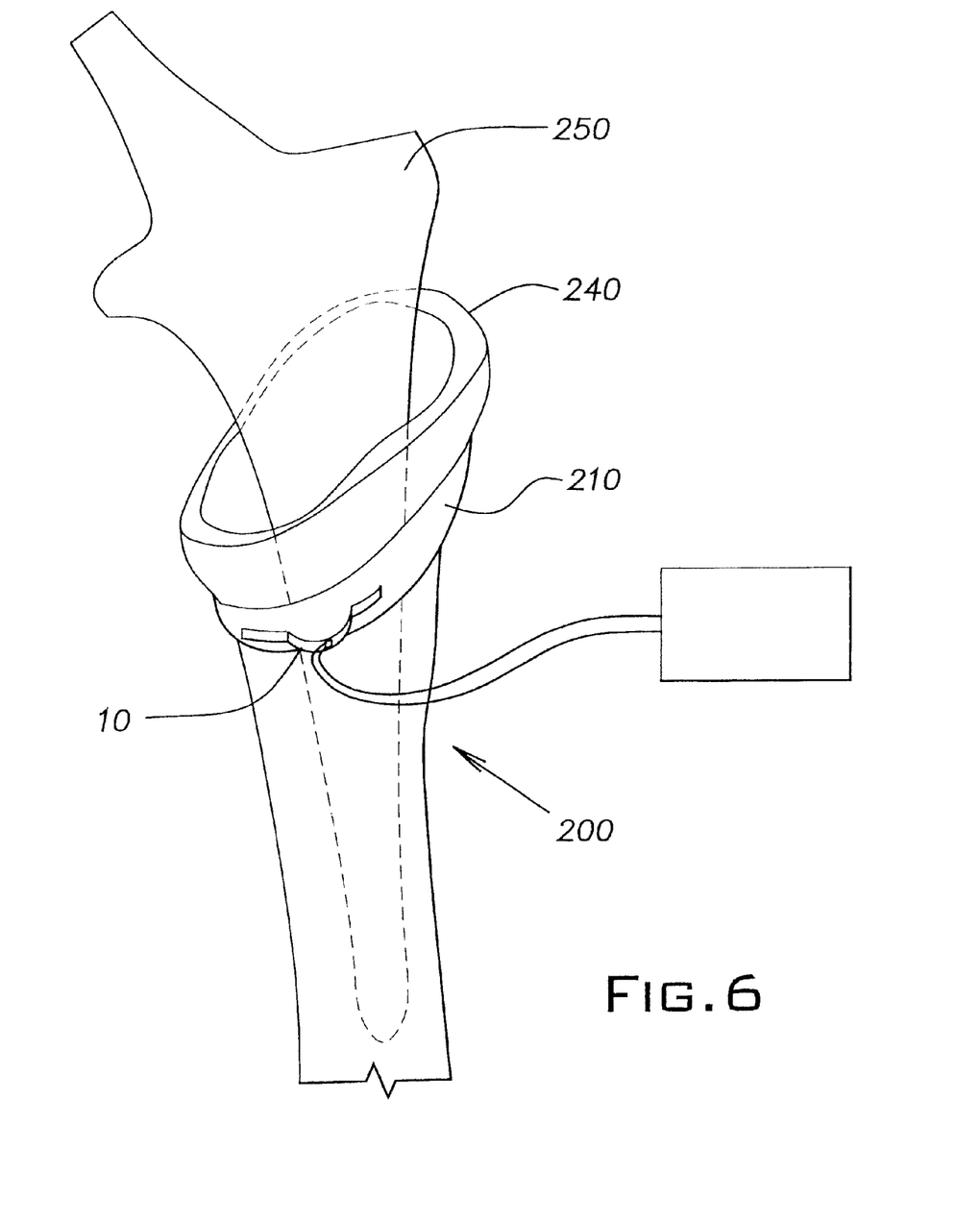
FIG. 6 shows a schematic of a hoop strain measuring device using a displacement transducer according to the first preferred embodiment of the invention.

The invented transducer is especially useful in surgical applications, particularly orthopedic surgical applications. FIG. 6 shows a hoop strain device 200 using the invented displacement transducer 10. The device 200 has a flexible band 210 with an invented transducer 10 mounted thereto. The device 200 can be used to measure radial expansion of any bone. In FIG. 6, the device 200 is being applied to measure expansion of a femur during hip replacement surgery. In the figure, flexible band 210 encircles the remaining proximal femur 240 following head resection. The band 210 is equipped with two mounting pads which will locate the displacement transducer 10 for the recording of hoop strain during insertion of the prosthetic stem 250 into the femur 240. The band may be equipped with multiple mounting pads should hoop strain measurements be desired from other locations around the femoral circumference. A displacement transducer 10 is mounted on the mounting pads of the band and aligned co-axial to the mid-section of the band. The transducer 10 is secured using cyanoacrylate glue or other known means.

Insertion of a prosthetic femoral stem 250 during total hip replacement is accomplished by sequentially striking a preselected stem geometry into a pre-broached femoral canal. The sequential striking of the stem 250 is terminated when proper seating of the implant is achieved. Unfortunately, in approximately 1%–5% of cases the femur 240 is fractured upon stem insertion. Such a mishap will then require circular wiring of the femoral shaft in order to obtain sufficient stability for subsequent implant incorporation. The additional costs associated with this additional procedure are on the order of $1200 (20 minutes of operating room time at approximately $60/minute). The femoral hoop strain device 200 could be inserted and ready for use within 30 seconds and subsequently minimize the possibility of femoral stem fracture.

Figure 7:
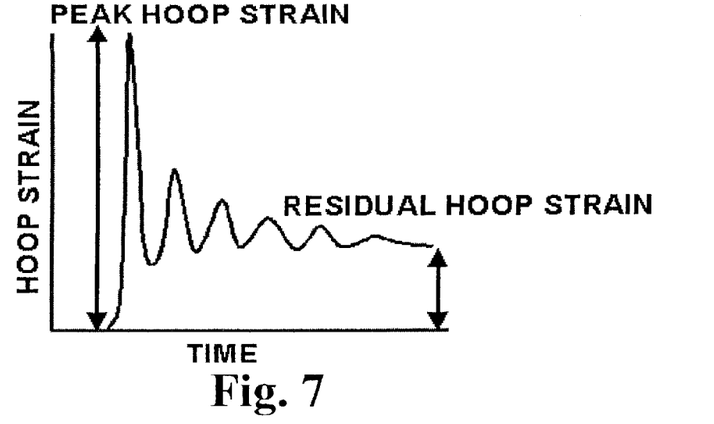
FIG. 7 shows a hoop strain profile for prosthesis insertion into the proximal end of a femur during hip replacement surgery.

The insertion of a femoral stem 250 into the proximal femur 240 causes the bone to expand. This is required in order to achieve a press fit between the prosthesis and the bone within the canal. During the striking process, the prosthesis is sequentially driven into an ever decreasing canal diameter. The striking of the prosthesis therefore will generate an increased hoop strain within the surrounding bone. Bone, as with all materials possesses elastic properties. Following the initial strike of the prosthesis, the bone will undergo stress relaxation around the prosthesis. The resulting strain profile is similar to that seen in FIG. 7. Following the initial peak hoop strain, the stress relaxation within the bone will result in a residual hoop strain from which the subsequent strike of the prosthesis will take place. Eventually the difference between the peak hoop strain generated within the bone during the prosthesis strike and the residual hoop strain following the strike will reach a critical value, at which point femoral fracture will occur. The transducer 10 is applied to accurately measure peak and residual hoop strain during prosthetic stem insertion to ensure the critical ratio of peak hoop strain to residual hoop strain is not reached so a fracture will be less likely to occur.

EXAMPLE 2

The invented transducer was compared with an Implantable Force Transducer (IFT) known in the art that was found in the literature. Below in Table 1 is a comparison of the IFT and the invented transducer based on the analysis established by Xu and Butler (Xu W S, Butler D L, Stouffer D C, Grood E S, Glos D L: Theoretical Analysis of an Implantable Force Transducer (ITF) for Tendon and Ligament Structures. Transactions of the ASME, Journal of Biomechanical Engineering, 114:170–177, 1992).

TABLE 1

Comparison of IFT and Invented Transducer

|  |  | IFT | Invented Transducer |
|---|---|---|---|
| Axial Load | p | 1 | 1 |
| Height | Hd | 2.2 mm | 4.37 mm |
| Thickness | Td | 0.254 mm | 0.01905 mm |
| Width | Wd | 6.5 mm | 5.44 mm |
| Modulus | E | 193.1 MPa | 105 MPa |
| Strain Output |  | 0.163 | 126.5 |
|  |  | = (6P × Hd)/(E × Wd × Td$^2$) | |
| Relative Output per Unit Load = (Invented)/(IFT) = 776 | | | |

This result demonstrates that for a given axial load, the invented transducer yielded a strain output approximately 776 times that of the reported IFT.

EXAMPLE 3

Figure 8:
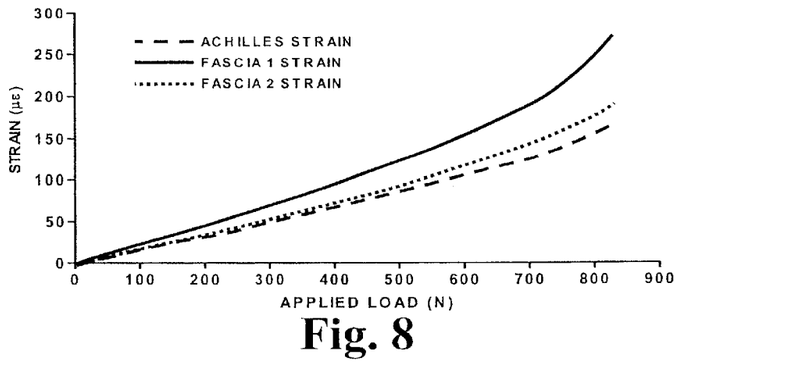
FIG. 8 is a plot showing the stress on the Achilles tendon and fascia of a human foot versus axial loading of the tibia as measured by three invented transducers.

Three invented transducers were applied to a human foot. The transducers had 10 mm diameter bridges 32 and utilized 0.015-inch strain gages mounted to 0.007 inch thick brass shim stock substrates. The transducers were 7–10 mm wide and were fastened to the respective ligaments described below using an adhesive. The transducers were placed within the foot with two on the fascia and one on the Achilles tendon. A compressive load was applied to the tibia using a hydraulic materials testing machine and the output of all three transducers simultaneously recorded with the results shown in FIG. 8. The transducers were calibrated such that 1 μm displacement=1 mV output, and the output was electronically scaled to read microstrains. As seen in FIG. 8, the output of all three transducers was linear with respect to the applied load except near the yield point of the ligaments.

EXAMPLE 4

Figure 9:
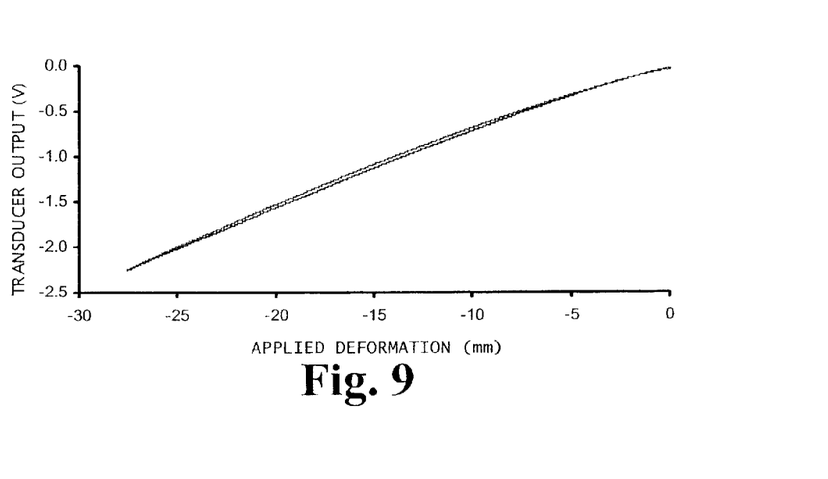
FIG. 9 is a plot showing the displacement of a cadaveric human spine in response to an applied bending load as measured by an invented transducer.

A single transducer was applied into a cadaveric human spine which spanned the gap occupied by an intervertebral disc. A transducer with a radial arc of 10 mm diameter was utilized. The transducer employed a 0.015-inch strain gage mounted to a 0.005 inch thick brass shim stock substrate of 5 mm width. The transducer was fastened to the spine using pins placed through the mounting tabs of the substrate. A materials testing machine was used to produce an applied bending deformation across the intervertebral disc of the spine. The transducer output was calibrated and scaled as in Example 3, and the results are shown in FIG. 9. As seen from FIG. 9, the output voltage was substantially linear for applied bending deformation of the spine. (The 30 mm range shown in FIG. 9 was the displacement of the piston required to generate the corresponding bending load on the spine). This is significant considering that an equivalent strain gage alone applied to measure the same bending displacement would most likely have failed from mechanical stresses, and further would not have exhibited a linear output voltage over the entire 30 mm range.

It should be noted that the invented displacement transducer is not limited to physiologic or surgical applications. The transducer can, and is intended, to be used for any application requiring high resolution measurement of displacements or loads, particularly very small displacements or loads, whether from impact to a specimen, shear stress, mechanical fatigue, etc. A partial inclusive list of several such applications follows: cable tensioning, surface contour mapping, pipe diameter or circumference measurement, measurement of aircraft wing strain, measurement of vehicle suspension system strain, position and control feedback sensor for a feedback control system, micro load cells, pipette calibration, micro displacement transducer, biopsy indentation testing of tissue mechanical properties, calcified artery or vein detection, submarine hull changes, gun barrel heat expansion, pressure/contact sensor, landing gear suspension monitor, compact disc read/write head position controller, ski binding release mechanism, recoil mechanism for sport shoes, gear derailleurs on bicycles, load control on fitness equipment, etc. In these applications the displacement transducer is mounted or attached to the indicated specimen as previously described and measurements are taken, recorded and interpreted in accordance with techniques known to those of ordinary skill in the art.

Although the hereinabove described embodiments of the invention constitute the preferred embodiments, it should be understood that modifications can be made thereto without departing from the scope of the invention as set forth in the appended claims.

What is claimed is:

1. A displacement transducer comprising a substrate having an arc portion and a stain gage securely mounted to said arc portion, said strain gage exhibiting a signal-stress curve having an inflection point between a substantially linear signal-stress region thereof, where signal varies substantially linearly with stress, and an exponential signal-stress region thereof, where signal varies exponentially with stress, said inflection point corresponding with a preselected radius of curvature of said strain gage, said strain gage being in a pre-stressed condition and having a radius of curvature not larger than said preselected radius of curvature such that said strain gage operates in said exponential signal-stress region of said signal-stress curve.

2. A displacement transducer according to claim 1 comprising a substrate having an arc portion and a strain gage securely mounted to said arc portion, wherein said arc portion is a polyfaceted arc having at least 3 discrete facets.

3. A transducer according to claim 2, wherein said polyfaceted arc is a rectilinear arc having 3 facets.

4. A transducer according to claim 1, wherein said arc portion is a curved arc.

5. A transducer according to claim 4, wherein said strain gage is mounted to said curved arc at an apex thereof.

6. A transducer according to claim 4, wherein said curved arc is semicircular.

7. A transducer according to claim 6, wherein said semicircular arc has a resting radius of 2–10 mm.

8. A transducer according to claim 4, wherein said stain gage is curved to conform to the surface of said curved arc.

9. A transducer according to claim 4, said curved arc having a radius of 2–10 mm, said strain gage having a radius of curvature substantially equal to said curved arc.

10. A transducer according to claim 1, wherein said stain gage is mounted to said arc portion via soldering.

11. A transducer according to claim 1, said substrate having a mounting tab on each side of said arc portion, said arc portion extending upward from each of said mounting tabs.

12. A transducer according to claim 11, wherein said mounting tabs are formed integrally with said arc portion.

13. A transducer according to claim 11, wherein said transducer has an amplifier (a) attached on one or more of said mounting tabs, (b) attached as a part of one of said a mounting tabs, or (c) integrated into said strain gage.

14. A transducer according to claim 1, wherein said substrate is made from brass, said strain gage being made of brass or being substantially temperature compensated for brass.

15. A transducer according to claim 14, said substrate having a thickness of 0.0001–0.1 inches and a width of 0.01–0.5 inches.

16. A transducer according to claim 1, wherein said strain gage is 0.005–0.03 inches in lenght and has a resistance at rest of 1–1000ohms.

17. A transducer according to claim 17, wherein said strain gage is about 0.015 inches in length and has a resistance at rest of 120 ohms.

18. A transducer according to claim 1, wherein said substrate is metal.

19. A transducer according to claim 1, wherein said substrate is plastic.

20. A transducer according to claim 4, wherein said strain gage is curved to conform to the surface of said curved arc.

21. A transducer according to claim 1, said stain gage having a resistance of about 121 ohms at resting or zero displacement condition of said transducer.

22. A transducer according to claim 21, wherein said strain gage generates a non-zero voltage output signal at said resting or zero displacement condition of said transducer via a wheatstone bridge circuit.

23. A transducer according to claim 1, wherein said strain gage has a planar resting profile,.

24. A transducer according to claim 1, said transducer having a substantially linear output for measuring up to 300 μm positive displacement.

25. A transducer according to claim 1, wherein said transducer has a resolution for measuring displacement smaller than 5 μm.

26. A transducer according to claim 25, wherein said transducer has a resolution for measuring displacement smaller than 2 μm.

27. A transducer according to claim 1, said transducer having an overall length of 5–40 mm and an overall height of 1–25 mm.

28. A transducer according to claim 1, wherein said transducer has a mass less than 2 grams.

29. A transducer according to claim 1, said transducer being adapted to function as a load cell for measuring an applied load, said substrate being cylindrical and having a circular cross-section with a diameter of at least 0.5 inches.

30. A displacement transducer according to claim 1, said signal being a resistance signal.

31. A transducer according to claim 1, having an overall length of 8–12 mm and a height of 4–6 mm.

32. A transducer according to claim 1, having a mass of less than 0.3 grams.

33. A transducer according to claim 1, said transducer being effective to measure displacements at least 10 percent the lenght of said strain gage.

34. A displacement transducer comprising a substrate having an arc portion and a strain gage securely mounted to said arc portion, said strain gage exhibiting a signal-stress curve having an inflection point between a substantially linear signal-stress region thereof, where signal varies substantially linearly with stress, and an exponential signal-stress region thereof, where signal varies exponentially with stress, said inflection point corresponding with a preselected radius of curvature of said strain gage, said strain gage being mounted to said arc portion in a pre-stressed condition having a radius of curvature not larger than said preselected radius of curvature, wherein said strain gage generates a non-zero voltage output signal at a resting or zero displacement condition of said transducer via a Wheatstone bridge circuit.

35. A transducer according to claim 34, said substrate further comprising a mounting tab on each side of said arc portion, said arc portion extending from each of said mounting tabs, said mounting tabs being formed integrally with said arc portion.

36. A transducer according to claim 34, said substrate being made from brass, said strain gage being made of brass or being substantially temperature compensated for brass.

37. A transducer according to claim 34, said substrate having a substantially rectangular cross-section, a thickness of 0.005 inches and a width of 3–4 mm.

38. A transducer according to claim 34, said transducer having an amplifier (a) attached on one or more of said mounting tabs, (b) attached as a part of one of said mounting tabs, or (c) integrated into said stain gage.

39. A transducer according to claim 34, said strain gage having a planar resting profile.

40. A transducer according to claim 34, said transducer having a resolution for measuring displacement subtract than 5 μm.

41. A transducer according to claim 34, said Wheatstone bridge circuit comprising said stain gage and three resistors, each of said three resistors having substantially fixed resistance.

42. A transducer according to claim 34, having an overall length of 8–12 mm and a height of 4–6 mm.

43. A transducer according to claim 34, having a mass of less than 0.3 grams.

44. A transducer according to claim 34, having a resolution for measuring displacement of 1 μm.

45. A transducer according to claim 34, said transducer being effective to measure displacements at least 10 percent the length of said strain gage.

* * * * *

UNITED STATES PATENT AND TRADEMARK OFFICE
CERTIFICATE OF CORRECTION

PATENT NO. : 6,810,753 B2
DATED : November 2, 2004
INVENTOR(S) : Antonio Valdevit et al.

It is certified that error appears in the above-identified patent and that said Letters Patent is hereby corrected as shown below:

Title page,
Item [75], Inventors, after "Lyndhurst, OH (US)" add -- Brian Laakaniemi, Cleveland Heights, OH (US) --.

Column 6,
Line 39, delete "11197" and insert therefor -- 0.197 --.

Column 11,
Lines 17 and 21, delete "stain" and insert therefor -- strain --.
Line 40, delete "lenght" and insert therefor -- lenght --.
Line 42, delete "17" and insert therefor -- 16 --.
Lines 49-50, delete "A transducer according to claim 4, wherein said strain gage is curved to conform to the surface of said curved arc." and insert therefor -- A transducer according to claim 1, said substrate having a substantially retangular cross-section, a thickness of 0.005 inches and a width of 3-4 mm. --
Line 57, delete "wheatstone" and insert therefor -- Wheatstone --.

Column 12,
Line 45, delete "stain" and insert therefor -- strain --.
Line 51, delete "subtract" and insert therefor -- smaller --.
Line 54, delete "stain" and insert therefor -- strain --.

Signed and Sealed this

Twenty-eighth Day of June, 2005

JON W. DUDAS
*Director of the United States Patent and Trademark Office*